United States Patent
Kroll et al.

(10) Patent No.: US 8,200,330 B2
(45) Date of Patent: Jun. 12, 2012

(54) RESPONDING TO PARTIAL LEAD FAILURE IN AN IMPLANTABLE CARDIOVERTER DEFIBRILLATOR

(75) Inventors: Mark Kroll, Orono, MN (US); Gabriel A. Mouchawar, Valencia, CA (US); J. Christopher Moulder, Portland, CA (US); Andre Walker, Monte Serreno, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 12/781,716

(22) Filed: May 17, 2010

(65) Prior Publication Data

US 2010/0228307 A1 Sep. 9, 2010

Related U.S. Application Data

(62) Division of application No. 11/433,541, filed on May 12, 2006, now Pat. No. 7,747,320.

(51) Int. Cl.
*A61N 1/39* (2006.01)

(52) U.S. Cl. .......................................................... 607/7

(58) Field of Classification Search .................. 607/1–7, 607/8, 9, 27, 28
See application file for complete search history.

(56) References Cited

U.S. PATENT DOCUMENTS

| 4,595,009 | A  | * | 6/1986 | Leinders ........................... 607/5 |
| 5,549,646 | A  | * | 8/1996 | Katz et al. ........................ 607/8 |
| 5,720,767 | A  | * | 2/1998 | Amely-Velez ..................... 607/5 |
| 6,456,876 | B1 | * | 9/2002 | Kroll ................................ 607/4 |

* cited by examiner

*Primary Examiner* — Carl H Layno
*Assistant Examiner* — Roland Dinga

(57) ABSTRACT

An implanted cardioverter defibrillator (ICD) delivers an electrical therapy signal to the heart of a patient. When ventricular fibrillation or another condition of the heart requiring high voltage therapy is sensed, the therapy signal is delivered to the heart. When a partial short-circuit or other low impedance condition occurs, an over-current protection circuit will stop delivery of a shocking pulse. The ICD will then reduce the voltage of the shocking pulse and try again to deliver electrical therapy. This process is repeated until a voltage level is found that is able to deliver the electrical therapy without causing an over-voltage condition. Alternate lead configurations may also be tried in an attempt to find a signal path that is not affected by the low impedance or short-circuit condition.

3 Claims, 4 Drawing Sheets

RESPONDING TO PARTIAL LEAD FAILURE IN AN IMPLANTABLE CARDIOVERTER DEFIBRILLATOR

CROSS REFERENCE TO RELATED APPLICATIONS

This application is a divisional of U.S. patent application Ser. No. 11/433,541, filed May 12, 2006, is now U.S. Pat. No. 7,747,320.

BACKGROUND

1. Field of the Invention

The present invention relates generally to implantable cardioverter defibrillators (ICDs) and, more particularly, to preserving ICD functionality in the event of lead failure.

2. Background Art

An implantable cardiac device is a medical device that is implanted in a patient to monitor electrical activity of a heart and to deliver appropriate electrical and/or drug therapy, as required. Implantable cardiac devices include, for example, pacemakers, cardioverters, defibrillators, and the like. The term "implantable cardioverter defibrillator" or simply "ICD" is used hereinafter to refer to any implantable cardiac device.

The ICD includes one or more electrodes that interact with the heart. Before delivering a signal to the heart from the ICD via the electrodes, it is desirable to first check the state of a signal path to determine, for example, if a low impedance or short-circuit like condition exists. A short-circuit like condition can be caused by an electrode touching a housing of the ICD, possibly due to rubbing between the electrode and the housing that has damaged the electrode insulation; two electrodes touching because insulating material between them has worn through; subclavicular crushing of electrodes against each other; displacement or dislodgement of an electrode; and from other situations. Typically, if a short-circuit like condition exists in the signal path, conventional devices either switch to a different electrode configuration (in an effort to find a non short-circuit signal path) or simply stop delivery of the therapy signal to the heart (to prevent damage to the ICD output circuitry). There are times, however, when an effective, alternate lead configuration is not available. Furthermore, failing to deliver therapy can be problematic if the therapy signal was required to sustain a patient's life.

What is needed is a system and method that overcomes deficiencies of known systems.

SUMMARY

An implanted cardioverter defibrillator (ICD) delivers an electrical therapy signal to the heart of a patient. When ventricular fibrillation or another condition of the heart requiring high voltage therapy is sensed, the therapy signal (i.e., an electrical shocking pulse) is delivered to the heart. When a partial short-circuit or other low impedance condition occurs, an over-current protection circuit will stop delivery of the shocking pulse. The ICD will then reduce the voltage of the shocking pulse and try again to deliver electrical therapy. This process is repeated until a voltage level is found that is able to deliver the electrical therapy without causing an over-current condition. Alternate lead configurations may also be tried in an attempt to find a signal path that is not affected by the low impedance or short-circuit condition.

Further features, as well as the structure and operation of various embodiments are described in detail below with reference to the accompanying drawings.

BRIEF DESCRIPTION OF THE DRAWINGS/FIGURES

The accompanying drawings, which are incorporated herein and form a part of the specification, illustrate various embodiments and, together with the description, further serve to explain the principles of the embodiments and to enable a person skilled in the relevant art to make and use the embodiments.

The various embodiments will now be described with reference to the accompanying drawings. In the drawings, like reference numbers may indicate identical or functionally similar elements.

DETAILED DESCRIPTION

The following detailed description refers to the accompanying drawings that illustrate exemplary embodiments. Other embodiments are possible, and modifications may be made to the embodiments. Therefore, the following detailed description is not meant to limit. Rather, the scope of the invention is limited only by the appended claims.

It will be apparent to one of skill in the art that the one or more embodiments, as described below, may be implemented in many different embodiments of hardware, software, and/or firmware. Any actual software and/or hardware described herein is not limiting of the one or more embodiments. Thus, the operation and behavior of the one or more embodiments will be described with the understanding that modifications and variations of the embodiments are possible, given the level of detail presented herein.

Before describing the one or more embodiments in detail, it is helpful to describe an example environment. The present embodiments are useful in the environment of an implantable cardiac device (ICD) as described below.

Figure 1:
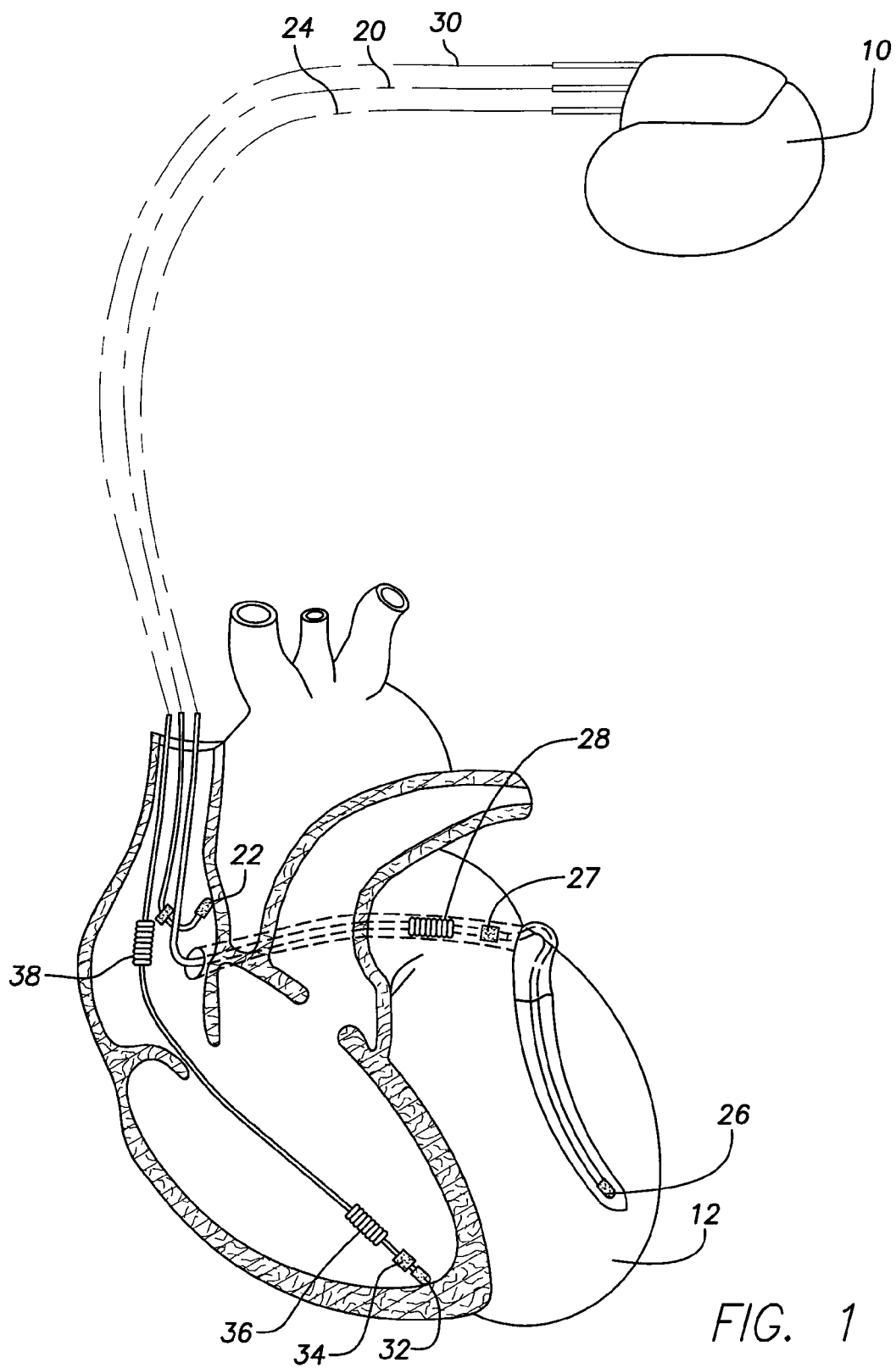
FIG. 1 is a diagram illustrating an ICD in electrical communication with at least three leads implanted into a patient's heart for delivering multi-chamber stimulation and shock therapy.

As shown in FIG. 1, an exemplary ICD 10 is in electrical communication with a patient's heart 12 by way of three leads, 20, 24 and 30, suitable for delivering multi-chamber stimulation and pacing therapy, according to one embodiment. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular (RV) lead 30 having, in this embodiment, a right ventricular tip electrode 32, a right ventricular ring electrode 34, a right ventricular coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the superior vena cava. Accordingly, right ventricular lead 30 is capable of receiving cardiac signals and delivering stimulation in the form of pacing and shock therapy to the right ventricle.

Figure 2:
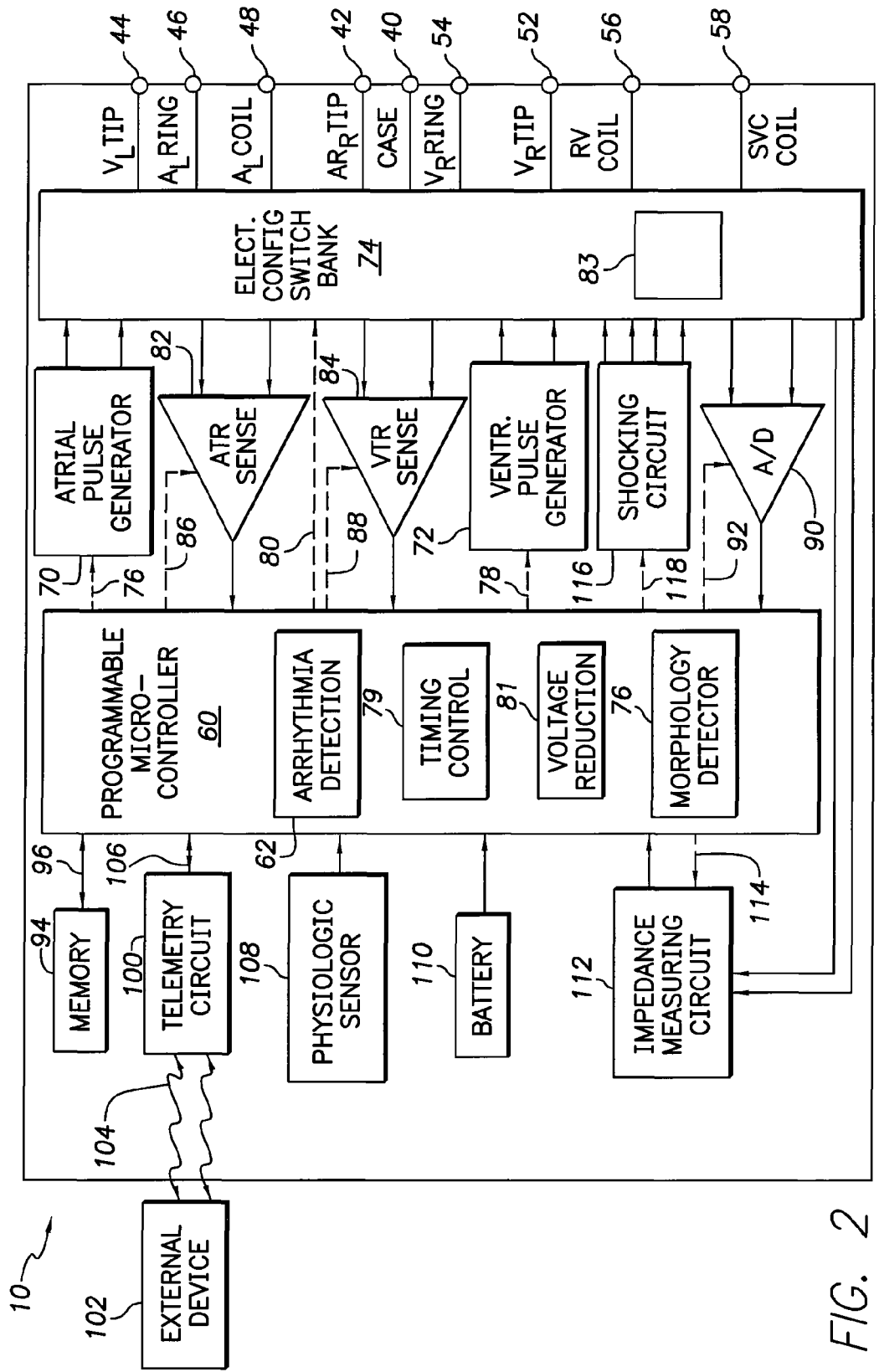
FIG. 2 is a block diagram of an ICD that can provide cardioversion, defibrillation and pacing stimulation in four chambers of a heart.

FIG. 2 shows a block diagram of ICD 10, which is capable of treating both fast and slow arrhythmias with stimulation therapy, including cardioversion, defibrillation, and pacing stimulation, according to one embodiment. While a particular multi-chamber stimulation device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case," or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

At the core of ICD 10 is a programmable microcontroller 60, which controls the various modes of stimulation therapy. As is well known in the art, microcontroller 60 typically includes a microprocessor, or equivalent control circuitry, designed specifically for controlling the delivery of stimulation therapy and can further include RAM or ROM memory, logic and timing circuitry, state machine circuitry, I/O circuitry, and the like. Typically, microcontroller 60 includes the ability to process or monitor input signals (data) as controlled by a program code stored in a designated block of memory. The details of the design of microcontroller 60 are not critical. Rather, any suitable microcontroller 60 can be used to carry out the functions described herein. The use of microprocessor-based control circuits for performing timing and data analysis functions are well known in the art.

Representative types of control circuitry that may be used include the microprocessor-based control system of U.S. Pat. No. 4,940,052 (Mann et. al.) and the state-machines of U.S. Pat. No. 4,712,555 (Thornander et al.) and U.S. Pat. No. 4,944,298 (Sholder). For a more detailed description of the various timing intervals used within the ICD's and their interrelationship, see U.S. Pat. No. 4,788,980 (Mann et. al.). The '052, '555, '298 and '980 patents are incorporated herein by reference in their entireties.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial fibrillation (AF) or ventricular fibrillation (VF). Such sensing circuits, 82 and 84, can be used to determine cardiac performance values.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation) are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detection circuitry 75 and morphology detection circuitry 76 to recognize and classify arrhythmia so that appropriate therapy can be delivered.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Data acquisition system 90 can be coupled to microcontroller 60, or other detection circuitry (not shown), for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Mann et al.), which patents are hereby incorporated herein by reference. The type of capture detection system used is not critical.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

The operating parameters of ICD 10 may be non-invasively programmed into memory 94 through a telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 can allow intracardiac electrograms and status information relating to the operation of ICD 10 (as contained in microcontroller 60 or memory 94) to be sent to external device 102 through an established communication link 104. Communication link 104 can be wired or wireless depending on a particular application, and both are contemplated.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

In one embodiment, ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.) in accordance with the embodiments. Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

ICD 10 further includes a magnet detection circuitry (not shown), coupled to microcontroller 60. The magnet detection circuitry detects the presence of a magnet placed outside the patient's body over ICD 10. A clinician may use the magnet to perform various test functions of ICD 10 and/or to signal microcontroller 60 that external device 102 is in place to receive or transmit data to microcontroller 60 through telemetry circuit 100.

As further shown in FIG. 2, ICD 10 is shown as having an impedance measuring circuit 112, which is enabled by microcontroller 60 via a control signal 114. For example, impedance can be measured as discussed in commonly owned U.S. Pat. No. 6,658,294 and in commonly owned, co-pending U.S. patent application Ser. No. 11/188,278, filed Jul. 21, 2005, which are incorporated herein by reference. Uses for an impedance measuring circuit 112 include, but are not limited to, lead impedance surveillance during the acute and chronic phases for proper lead positioning or for detecting dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves. The impedance measuring circuit 112 can be coupled to switch 74 so that any desired electrode may be used.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 116 (e.g., a signal generator) by way of a control signal 118. The shocking circuit 116 generates shocking pulses (e.g., signals or therapy signals) of low (e.g., up to about 0.5 joules), moderate (about 0.5 to about 10 joules), or high energy (about 11 to about 40 joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized to be recognized), and pertaining exclusively to the treatment of fibrillation. Accordingly, microcontroller 60 is capable of controlling the synchronous or asynchronous delivery of the shocking pulses.

ICD 10 additionally includes a first power system 110 (e.g., a battery), which provides operating power to a load that includes most of the circuits shown in FIG. 2. Because ICD 10 employs shocking therapy, battery 110 must be capable of operating at low current drains for long periods of time, and then be capable of providing high-current pulses (for capacitor charging) when the patient requires a shock pulse. Because the lower current drains occur over much longer periods of time than the higher current drains, the lower current drains typically account for a significant portion of battery 110 consumption. Elective replacement time of battery 110 may be determined by monitoring the level of battery 110 depletion. Battery 110 may be a lithium/silver vanadium oxide battery but other battery chemistries can also be used.

In the event of an arrhythmic event such as ventricular fibrillation (VF), it is desired to immediately provide shocking therapy to defibrillate the heart. However, as discussed above, it is undesirable to deliver a large shocking pulse into leads that are short-circuited together. Impedance measuring circuit 112 can be used to measure the impedance of a particular lead configuration prior to delivery of a shock. Such monitoring can be used to find both short-circuits and open-circuits.

In addition to using impedance measuring circuit 112 to monitor the impedance between a particular electrode combination, an over-current protection circuit 83 is used to protect shocking circuit 116 and electrically configurable switch 74 from damage caused by delivering high voltage shocking pulse into short-circuited leads. For example, over-current protection circuit 83 can monitor the current being delivered to the leads and stop current deliver (i.e., open the circuit) if the current exceeds a preset value, such as 40 amperes. The over-current protection circuit can detect the over-current condition and stop current flow in, for example, about 100 microseconds. This quick response will prevent any damage to ICD 10.

In FIG. 2, over-current protection circuit 83 is shown as being part of switch 74. In another example, over-current protection circuit 83 can be part of shocking circuit 116. Such over-current protection circuits are known and would be apparent to a person skilled in the relevant arts.

As discussed above, upon detection of a short-circuit condition, known ICD's either switch to a different lead configuration (in an attempt to find non-short-circuited leads) or simply fail to deliver the required shocking therapy. Alternate lead configurations, however, may not be available or may not be as effective in delivering the required electrical therapy. Furthermore, failing to deliver a required electrical therapy can be problematic.

To overcome these limitations, ICD 10 includes voltage reduction circuitry 81. Voltage reduction circuitry 81 is shown in FIG. 2 as being part of micro-controller 60. Voltage reduction circuitry 81 may be implemented in software, firmware, hardware or any combination thereof. Furthermore, voltage reduction circuitry 81 can be part of microcontroller 60, a separate functional block of ICD 10 or may be, for example, part of shocking circuit 116.

In the event that over-current protection circuit 83 detects an over-current condition, circuit 83 will stop full delivery of the electrical pulse to the selected leads. Thereafter, voltage reduction circuit 81 will attempt to find a reduced voltage of the therapy signal that will avoid an over-current condition but still deliver effective therapy to the heart.

Finding a reduced voltage that will not result in an over-current condition is premised on the fact that many seemingly "short-circuit" conditions are actually caused by low conductor spacings at either thin or nonexistent insulation that are not total or complete short-circuits. That is, the impedance (resistance) of the signal path through the selected lead/electrode configuration is high until a critical "arc-over" voltage is presented. For example, subclavicular crushing or rubbing between an electrode and the ICD housing or between two leads can damage the electrode insulation, causing a lower than normal spacing (e.g., a "conditional" short-circuit) but not causing a continuous short-circuit. In these cases of less than normal spacing or insulation, a shocking pulse at a high voltage (e.g., 870 volts) may cause an over current condition, while a shocking pulse at a lower voltage (e.g., 470 volts) may not cause an over current condition. If a therapeutically effective shocking pulse can be delivered using a lower voltage, then a good result has been achieved. In some cases, the lower voltage pulse could result in defibrillation of a heart that otherwise might not receive the required therapy.

Figure 3:
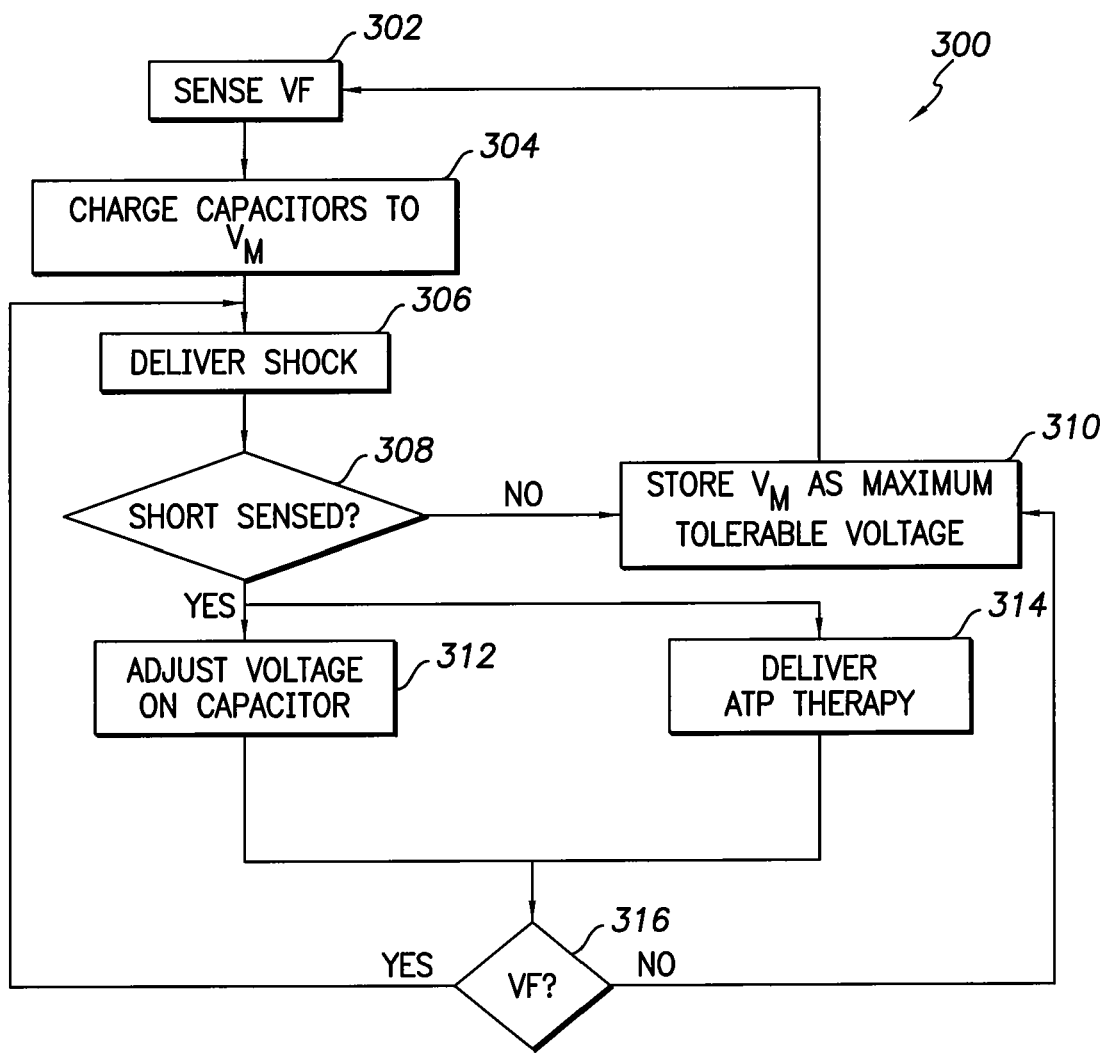
FIG. 3 is a flowchart illustrating operation of an ICD according to one embodiment.

Example operation of voltage reduction circuitry 81 of ICD 10 is illustrated in a method 300 shown in the flowchart of FIG. 3. Referring to FIG. 3, an arrhythmia, such as ventricular fibrillation (VF), is sensed by ICD 10 as indicated at step 302. ICD 10 then determines that shocking therapy is required to treat the VF. In a step 304, capacitors within ICD 10 are charged to a relatively high voltage ($V_M$) in order to store the energy required to deliver the required shock. For example, two series connected capacitors in shocking circuit 116 are charged to a total of 870 volts.

In step 306, shocking circuit 116 delivers the shocking pulse to the selected lead electrodes via switch 74. If over-current protection circuit 83 senses an over-current condition at step 308, then circuit 83 will terminate delivery of the full shocking pulse (e.g., circuit 83 can respond in about one (1) microsecond). The method then proceeds to step 312.

At step 312, the voltage on the capacitors is adjusted to a smaller voltage magnitude. For example, in the case where the capacitors were charged to 870 volts and an over-current condition was detected before the full charge was delivered, the majority of the charge will still remain on the capacitors. Therefore, the capacitors may need to be further discharged to achieve a smaller voltage magnitude. For example, the capacitors could be discharged (as necessary) to a value of 770 volts, 100 volts less than the full charge value. In other instances, it may be necessary to charge the capacitors to achieve the desired voltage magnitude. In one embodiment, the method could then proceed directly to step 306, where shocking circuit 116 delivers the reduced-voltage shocking pulse to the selected lead electrodes. In another embodiment, optional steps 314 and 316 may be performed.

Step 314 is performed substantially in parallel with step 312. That is, while the voltage on the capacitors is adjusted in step 312, ATP (anti-tachycardia pacing) therapy is delivered at step 314. The ATP therapy may use the currently selected electrode configuration or may use a different electrode configuration. For example, this can include biventricular ATP with various schemas and can also include ATP between large electrodes. Use of ATP therapy to treat VF is premised on the observation that oftentimes an indicated VF is actually tachycardia. Next, once step 312 is complete, a check is made at step 316 to determine whether VF is still present. If VF is no longer present, the method proceeds to step 310.

Returning to step 308, if no over-current condition is sensed at step 308, then the method proceeds to step 310. At step 310, the voltage across the capacitors ($V_M$) is stored. The assumption is that, since the voltage $V_M$ did not result in an over-current condition, the value of $V_M$ is the maximum voltage that can be delivered without causing an over-current condition.

In method 300, steps 306-316 may be performed in an iterative manner. For example, an initial 870 volt shocking pulse may cause an over-current condition (steps 306 and 308). The voltage on the capacitors may then be reduced to 770 volts (step 312) and another shock delivered at step 306. If this 770 volts pulse again causes an over-current condition (step 308), the voltage can be reduced to 670 volts (step 312) and another shock delivered. If the 670 Volt shock does not cause an over-current condition, then the 670 Volt value can be saved (step 310) as a value that will not cause an over-current condition. The method can then return to step 302 where it will end if VF is no longer present. However, if VF is present, the capacitors can be charged to the stored 670 Volt value, and another shock can be delivered.

In one embodiment of the invention, the capacitor voltage ($V_M$) is decreased in steps of about 100 volts. In another embodiment, the capacitor voltage is decreased in steps of about 10 volts. It will be apparent to a person skilled in the art that various other voltage steps sizes can be used, including values between 10 volts and 100 volts. It will also be apparent to a person skilled in the art that large steps will result in a method that will more quickly execute, and that smaller steps will allow ICD 10 to more closely identify the actual value of the voltage that avoids an over-current condition (if such a voltage exists). The actual voltage step size is a design choice depending on a variety of factors and may be programmably selected via an external programmer 102. In one alternative embodiment, a binary search is used to quickly determine the highest safe voltage.

Figure 4:
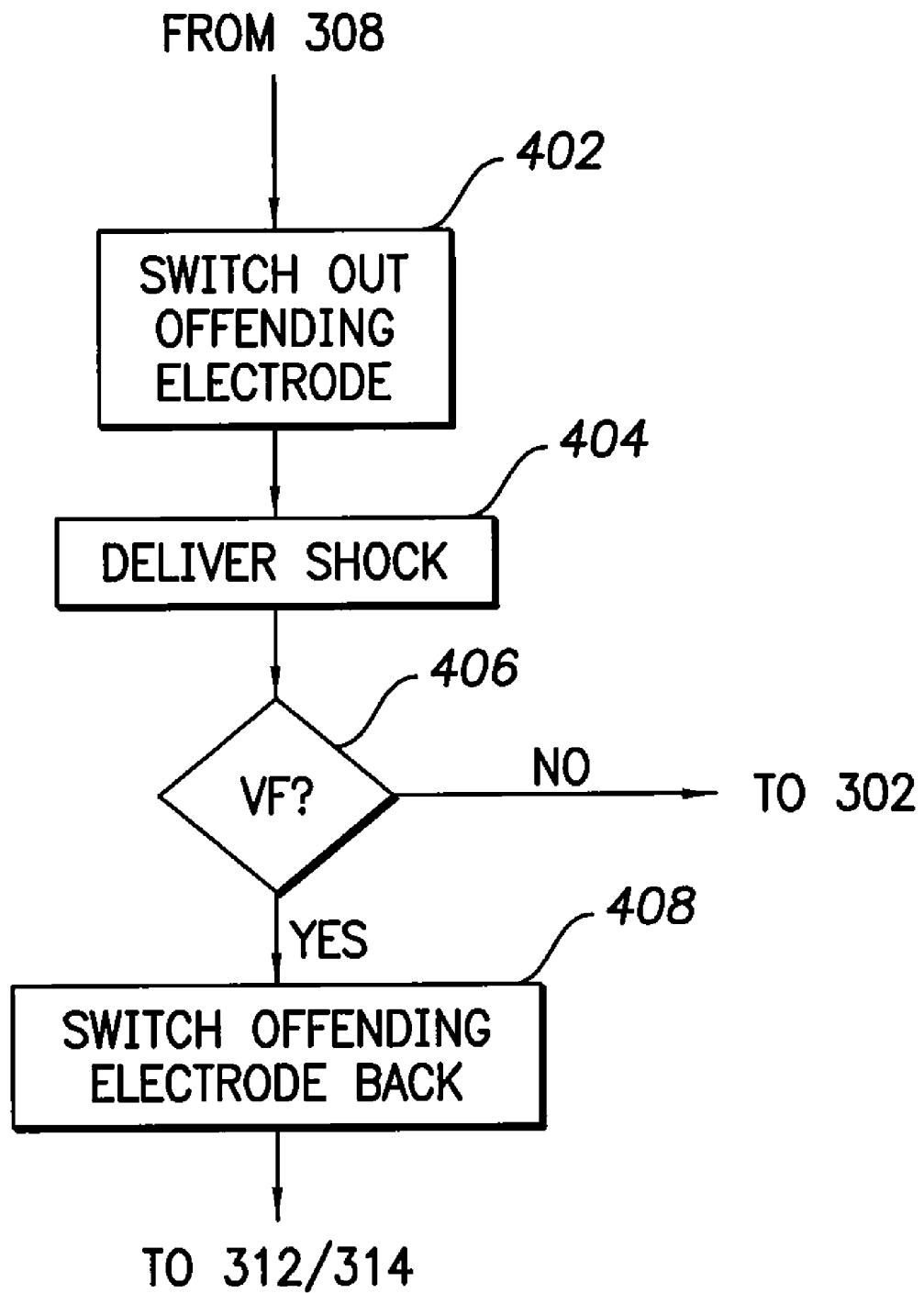
FIG. 4 is an extension of the flowchart of FIG. 3, illustrating an alternate embodiment.

FIG. 4 shows an alternate embodiment of method 300 shown in FIG. 3. In this alternate embodiment, steps 402-408 are added into method 300 between steps 308 and 312/314. In this alternate embodiment, after an over-current condition is sensed in step 308, the method proceeds to step 402. In step 402, an "offending" electrode (i.e., the electrode that is believed to have contributed to the short-circuit condition) is switched out of the signal path. In other words, a new electrode configuration is selected. Switching the "offending" electrode out of the signal path can be done with one or more methods as described in commonly owned, co-pending U.S. patent application Ser. No. 11/188,278. For example, if the shock of step 306 was delivered to the heart via a path that uses RV coil electrode 56 as the anode and case 40 as the cathode, then case 40 could be replaced with a different electrode, such as SVC coil electrode 58. Switching the electrode configuration in this manner may remove the low-impedance condition that tripped over-current protection circuit 83. Thereafter, the method proceeds to step 404.

In a step 404, shocking circuit 116 delivers a shocking pulse (e.g., at a full capacitor voltage or at a reduced voltage $V_M$) to the selected lead electrodes via switch 74. In a step 406, it is determined whether the shock was successful in terminating the VF. If VF is no longer present, then the method returns to step 302 to monitor for further arrhythmias. If VF is still present, the therapy delivered via the new lead configuration was not successful, so the method proceeds to step 408 where the original, offending lead configuration is reselected. The method then proceeds to steps 312 and 314 as described above.

In yet another embodiment of the invention, step 408 can be omitted, and method 300 can proceed using the newly selected electrode configuration. In yet another embodiment, method 300 can proceed (without steps 402-408) until the voltage $V_M$ is reduced to a predetermined minimum voltage (e.g., 200 volts) without finding a voltage that would not cause an over-current condition. Thereafter, step 402 could be performed to select an alternate electrode configuration. Method 300 could then be repeated using the alternate electrode configuration.

Example embodiments of the methods, systems, and components of the have been described herein. As noted elsewhere, these example embodiments have been described for illustrative purposes only, and are not intended to limit the scope of the present invention. Other embodiments are possible. Such embodiments will be apparent to persons skilled in the relevant art(s) based on the teachings contained herein. Thus, the breadth and scope of the invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

What is claimed is:

1. An implantable cardioverter defibrillator, comprising:
   means for sensing an arrhythmic event from the heart;
   means for delivering an initial shock signal to the heart;
   means for detecting an over-current condition and for discontinuing delivery of the initial shock signal prior to delivery of the complete initial shock signal if an over-current condition is detected; and means for reducing the voltage of a second shock signal and delivering the reduced voltage second shock signal when the initial shock signal results in an over-current condition.

2. The implantable cardioverter defibrillator of claim 1, further comprising:

means for delivering anti-tachycardia pacing while the voltage of the initial shock signal is reduced by the reducing means.

3. An implantable medical device for delivering an electrical signal to a heart of a patient, comprising:

a shocking circuit having one or more shock capacitors that generates a therapy signal; and a microcontroller to control delivery of the therapy signal to the heart, wherein the microcontroller is configured to discontinue delivery of an initial shock signal prior to delivery of the complete initial shock signal if the implantable device senses a current that exceeds a predetermined threshold, the microcontroller being further configured to then successively adjust the voltage on the one or more shock capacitors to reduce the voltage of one or more subsequent lower voltage shocks prior to the delivery of the one or more subsequent lower voltage shocks when an over-current condition is detected until a capacitor voltage is identified at which the over-current condition is avoided.

* * * * *